(12) United States Patent
Warner et al.

(10) Patent No.: US 8,884,081 B2
(45) Date of Patent: Nov. 11, 2014

(54) INTEGRATED PROCESS FOR PRODUCING ACETIC ACID AND ALCOHOL

(75) Inventors: R. Jay Warner, Houston, TX (US); Victor J. Johnston, Houston, TX (US); David Lee, Seabrook, TX (US); Manuel Salado, Seabrook, TX (US); Mark O. Scates, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 176 days.

(21) Appl. No.: 13/094,661

(22) Filed: Apr. 26, 2011

(65) Prior Publication Data
US 2012/0277481 A1    Nov. 1, 2012

(51) Int. Cl.
| C07C 31/08 | (2006.01) |
| C07C 67/08 | (2006.01) |
| C07C 29/90 | (2006.01) |
| C07C 29/149 | (2006.01) |
| C07C 29/80 | (2006.01) |

(52) U.S. Cl.
CPC ............... *C07C 29/90* (2013.01); *C07C 67/08* (2013.01); *C07C 29/149* (2013.01); *C07C 29/80* (2013.01)
USPC ............ 568/890; 568/881; 568/884; 568/885

(58) Field of Classification Search
None
See application file for complete search history.

(56) References Cited

U.S. PATENT DOCUMENTS

| | | |
|---|---|---|
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,769,329 A | 10/1973 | Paulik |
| 3,990,952 A | 11/1976 | Katzen et al. |
| 4,126,539 A | 11/1978 | Derr, Jr. et al. |
| 4,149,940 A | 4/1979 | Pinto |
| 4,275,228 A | 6/1981 | Gruffaz |
| 4,306,942 A | 12/1981 | Brush |
| 4,317,918 A | 3/1982 | Takano |
| 4,319,058 A | 3/1982 | Kulprathipanja |
| 4,352,940 A | 10/1982 | Adelman et al. |
| 4,379,028 A | 4/1983 | Berg |
| 4,395,576 A | 7/1983 | Kwantes |
| 4,398,039 A | 8/1983 | Pesa |
| 4,421,939 A | 12/1983 | Kiff |
| 4,422,903 A | 12/1983 | Messick |
| 4,443,639 A | 4/1984 | Pesa et al. |
| 4,454,358 A | 6/1984 | Kummer |
| 4,465,854 A | 8/1984 | Pond |
| 4,471,136 A | 9/1984 | Larkins |
| 4,480,115 A | 10/1984 | McGinnis |
| 4,492,808 A | 1/1985 | Hagen |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer |
| 4,615,806 A | 10/1986 | Hilton |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,886,905 A | 12/1989 | Larkins et al. |
| 4,908,477 A | 3/1990 | Hartmann et al. |
| 4,961,826 A | 10/1990 | Grethlein |
| 4,978,778 A | 12/1990 | Isshiki et al. |
| 4,985,572 A | 1/1991 | Kitson |
| 4,990,655 A | 2/1991 | Kitson |
| 4,994,608 A | 2/1991 | Torrence |
| 5,001,259 A | 3/1991 | Smith |
| 5,026,908 A | 6/1991 | Smith |
| 5,035,776 A | 7/1991 | Knapp |
| 5,061,671 A | 10/1991 | Kitson |
| 5,070,016 A | 12/1991 | Hallberg et al. |
| 5,124,004 A | 6/1992 | Grethlein |
| 5,139,981 A | 8/1992 | Kurland |
| 5,144,068 A | 9/1992 | Smith |
| 5,149,680 A | 9/1992 | Kitson |
| 5,185,481 A | 2/1993 | Muto |
| 5,198,592 A | 3/1993 | Van Beijnum et al. |
| 5,215,902 A | 6/1993 | Tedder |
| 5,227,141 A | 7/1993 | Kim |

(Continued)

FOREIGN PATENT DOCUMENTS

| | | |
|---|---|---|
| CN | 201768393 | 3/2011 |
| CN | 102228831 | 11/2011 |
| CN | 102229520 | 11/2011 |
| EP | 0056488 | 7/1982 |
| EP | 0104197 | 4/1984 |

(Continued)

OTHER PUBLICATIONS

Xu, et al., "Kinetics of Acetic Acid Esterification over Ion Exchange Catalysts", Canadian Journal of Chemical Engineering, vol. 74, Aug. 1, 1996, pp. 493-500.

Ragaini V, et al., "Increasing the value of dilute acetic acid streams through esterification", Applied Catalysis B: Environmental, vol. 64, No. 1-2, Apr. 18, 2006, pp. 66-71.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

(Continued)

*Primary Examiner* — Sudhakar Katakam

(57) ABSTRACT

The present invention relates generally to processes for producing ethanol and acetic acid and, in particular, to a process for integrating an ethanol production process with an acetic acid production process.

18 Claims, 2 Drawing Sheets

(56) References Cited

U.S. PATENT DOCUMENTS

| | | |
|---|---|---|
| 5,233,099 A | 8/1993 | Tabata |
| 5,237,108 A | 8/1993 | Marraccini |
| 5,250,271 A | 10/1993 | Horizoe |
| 5,348,625 A | 9/1994 | Berg |
| 5,414,161 A | 5/1995 | Uhm et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli |
| 5,502,248 A | 3/1996 | Funk et al. |
| RE35,377 E | 11/1996 | Steinberg |
| 5,599,976 A | 2/1997 | Scates |
| 5,696,284 A | 12/1997 | Baker |
| 5,731,252 A | 3/1998 | Warner |
| 5,762,765 A | 6/1998 | Berg |
| 5,770,770 A | 6/1998 | Kim |
| 5,800,681 A | 9/1998 | Berg |
| 5,821,111 A | 10/1998 | Grady |
| 5,861,530 A | 1/1999 | Atkins et al. |
| 5,877,347 A | 3/1999 | Ditzel |
| 5,877,348 A | 3/1999 | Ditzel |
| 5,883,295 A | 3/1999 | Sunley |
| 5,932,764 A | 8/1999 | Morris |
| 5,942,460 A | 8/1999 | Garland |
| 5,973,193 A | 10/1999 | Crane et al. |
| 5,993,610 A | 11/1999 | Berg |
| 6,040,474 A | 3/2000 | Jobson et al. |
| 6,093,845 A | 7/2000 | Van Acker et al. |
| 6,121,498 A | 9/2000 | Tustin |
| 6,143,930 A | 11/2000 | Singh |
| 6,232,352 B1 | 5/2001 | Vidalin |
| 6,294,703 B1 | 9/2001 | Hara |
| 6,326,515 B1 | 12/2001 | Clode et al. |
| 6,339,171 B1 | 1/2002 | Singh |
| 6,375,807 B1 | 4/2002 | Nieuwoudt |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser |
| 6,627,770 B1 | 9/2003 | Cheung |
| 6,632,330 B1 | 10/2003 | Colley et al. |
| 6,657,078 B2 | 12/2003 | Scates |
| 6,685,754 B2 | 2/2004 | Kindig |
| 6,693,213 B1 | 2/2004 | Kolena |
| 6,696,596 B1 | 2/2004 | Herzog et al. |
| 6,723,886 B2 | 4/2004 | Allison |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,906,228 B2 | 6/2005 | Fischer |
| 6,927,048 B2 | 8/2005 | Verser |
| 7,005,541 B2 | 2/2006 | Cheung |
| 7,074,603 B2 | 7/2006 | Verser |
| 7,084,312 B1 | 8/2006 | Huber et al. |
| 7,115,772 B2 | 10/2006 | Picard |
| 7,208,624 B2 | 4/2007 | Scates |
| 7,223,886 B2 | 5/2007 | Scates |
| 7,297,236 B1 | 11/2007 | Vander Griend |
| 7,351,559 B2 | 4/2008 | Verser |
| 7,399,892 B2 | 7/2008 | Rix et al. |
| 7,507,562 B2 | 3/2009 | Verser |
| 7,553,397 B1 | 6/2009 | Colley |
| 7,572,353 B1 | 8/2009 | Vander Griend |
| 7,588,690 B1 | 9/2009 | Tsao |
| 7,601,865 B2 | 10/2009 | Verser |
| 7,608,744 B1 | 10/2009 | Johnston |
| 7,682,812 B2 | 3/2010 | Verser |
| 7,700,814 B2 | 4/2010 | Garton et al. |
| 7,718,039 B2 | 5/2010 | Dirkzwager et al. |
| 7,732,173 B2 | 6/2010 | Mairal et al. |
| 7,744,727 B2 | 6/2010 | Blum |
| 7,834,223 B2 | 11/2010 | Atkins |
| 7,842,844 B2 | 11/2010 | Atkins |
| 7,863,489 B2 | 1/2011 | Johnston |
| 7,884,253 B2 | 2/2011 | Stites |
| 7,888,082 B2 | 2/2011 | Verser |
| 7,906,680 B2 | 3/2011 | Scates et al. |
| 7,947,746 B2 | 5/2011 | Daniel et al. |
| 2003/0013908 A1 | 1/2003 | Horan et al. |
| 2003/0077771 A1 | 4/2003 | Verser et al. |
| 2006/0019360 A1 | 1/2006 | Verser |
| 2006/0127999 A1 | 6/2006 | Verser |
| 2006/0252956 A1 | 11/2006 | Miller et al. |
| 2007/0031954 A1 | 2/2007 | Mairal et al. |
| 2007/0106246 A1 | 5/2007 | Modesitt |
| 2007/0270511 A1 | 11/2007 | Melnichuk |
| 2008/0135396 A1 | 6/2008 | Blum |
| 2008/0193989 A1 | 8/2008 | Verser |
| 2008/0207953 A1 | 8/2008 | Houssin et al. |
| 2008/0287706 A1 | 11/2008 | Powell |
| 2008/0293966 A1 | 11/2008 | Scates |
| 2009/0005588 A1 | 1/2009 | Hassan et al. |
| 2009/0014313 A1 | 1/2009 | Lee |
| 2009/0023192 A1 | 1/2009 | Verser |
| 2009/0069609 A1 | 3/2009 | Kharas |
| 2009/0081749 A1 | 3/2009 | Verser |
| 2009/0107833 A1 | 4/2009 | Warner |
| 2009/0166172 A1 | 7/2009 | Casey |
| 2009/0221725 A1 | 9/2009 | Chorney et al. |
| 2009/0270651 A1 | 10/2009 | Zinobile |
| 2009/0281354 A1 | 11/2009 | Mariansky |
| 2009/0299092 A1 | 12/2009 | Beavis et al. |
| 2009/0318573 A1 | 12/2009 | Stites |
| 2009/0326080 A1 | 12/2009 | Chornet et al. |
| 2010/0016454 A1 | 1/2010 | Gracey et al. |
| 2010/0029980 A1 | 2/2010 | Johnston |
| 2010/0029995 A1 | 2/2010 | Johnston |
| 2010/0030001 A1 | 2/2010 | Chen |
| 2010/0030002 A1 | 2/2010 | Johnston |
| 2010/0121114 A1 | 5/2010 | Weiner |
| 2010/0130775 A1 | 5/2010 | Voss et al. |
| 2010/0137630 A1 | 6/2010 | Garton et al. |
| 2010/0197485 A1 | 8/2010 | Johnston |
| 2010/0197985 A1 | 8/2010 | Johnston et al. |
| 2010/0204512 A1 | 8/2010 | Kimmich et al. |
| 2011/0004033 A1 | 1/2011 | Johnston et al. |
| 2011/0046421 A1 | 2/2011 | Daniel et al. |
| 2011/0082322 A1 | 4/2011 | Jevtic et al. |
| 2011/0190547 A1 | 8/2011 | Jevtic et al. |
| 2011/0190548 A1 | 8/2011 | Jevtic et al. |
| 2011/0275861 A1 | 11/2011 | Johnston et al. |
| 2011/0275862 A1 | 11/2011 | Johnston et al. |
| 2012/0010438 A1 | 1/2012 | Lee et al. |
| 2012/0010445 A1 | 1/2012 | Johnston et al. |
| 2012/0010447 A1 | 1/2012 | Warner et al. |
| 2012/0273338 A1 | 11/2012 | Warner |

FOREIGN PATENT DOCUMENTS

| | | |
|---|---|---|
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0990638 | 4/2000 |
| EP | 2060553 | 5/2009 |
| EP | 2060553 A1 * | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| JP | 6-116182 | 4/1994 |

(56) References Cited

FOREIGN PATENT DOCUMENTS

| JP | 2001-046874 | 2/2001 |
|---|---|---|
| WO | 8303409 | 10/1983 |
| WO | WO 02/092541 | 11/2002 |
| WO | WO 2005/102513 | 11/2005 |
| WO | WO 2007/003897 | 1/2007 |
| WO | 2008135192 | 11/2008 |
| WO | 2009009322 | 1/2009 |
| WO | 2009009323 | 1/2009 |
| WO | WO 2009/009320 | 1/2009 |
| WO | 2009048335 | 4/2009 |
| WO | 2009063176 | 5/2009 |
| WO | WO 2009/063174 | 5/2009 |
| WO | WO 2009/105860 | 9/2009 |
| WO | WO 2010/014151 | 2/2010 |
| WO | 2010055285 | 5/2010 |
| WO | WO 2011/053365 | 5/2011 |
| WO | WO 2012/006236 | 1/2012 |
| WO | WO 2012/006388 | 1/2012 |

OTHER PUBLICATIONS

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2012), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Subramani et al., "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Witzeman and Agreda, "Safety and Performance Assessment of Ethanol/Diesel Blends (e-blend)" NREL/SR-540-34817, at p. 1-1, Sep. 2003.

H. Constantin et al., "Influence of C-Sources on the Denitrification Rate of a High-Nitrate Concentrated Industrial Wastewater", Wat. Res., 1997, vol. 31, No. 3, pp. 583-589.

International Search Report and Written Opinion for PCT/US2011/059917 mailed Jul. 23, 2012.

International Search Report and Written Opinion for PCT/US2011/059887 mailed May 29, 2012.

International Search Report and Written Opinion for PCT/US2011/060014 mailed Jun. 29, 2012.

International Search Report and Written Opinion for PCT/US2011/023276 mailed Sep. 2, 2011.

International Written Opinion for PCT/US2011/023276 mailed May 8, 2012.

International Search Report and Written Opinion for PCT/US2012/035203 mailed Jul. 11, 2012.

International Search Report and Written Opinion for PCT/US2011/059909 mailed Jul. 30, 2012.

Jones, J. H., "The Cativa Process for the Manufacture of Acetic Acid", Platinum Metals Review, 44 (3), pp. 94-105 (2000).

Michael Gauβ, et al., Applied Homogeneous Catalysis with Organometallic Compounds: A Comprehensive Handbook in Volume Two, Chapter 2.1, p. 27-200, (1st ed., 1996).

Office Action for U.S. Appl. No. 13/094,657 dated Aug. 27, 2013.

Response to Office Action for U.S. Appl. No. 13/094,657, filed Dec. 27, 2013.

Office Action for corresponding Chinese Appl. No. 201180042198.4 dated Mar. 5, 2014.

* cited by examiner

US 8,884,081 B2

INTEGRATED PROCESS FOR PRODUCING ACETIC ACID AND ALCOHOL

FIELD OF THE INVENTION

The present invention relates generally to integrated processes for producing acids and alcohols and, in particular, to a process for integrating an ethanol production process with an acetic acid production process.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

In addition, when conversion is incomplete, unreacted acid remains in the crude ethanol product, which must be removed to recover ethanol. Other processes, such as those described in U.S. Pat. No. 5,599,976, involve a process for treating aqueous streams comprising up to 50 wt. % acetic acid in a catalytic distillation unit to react the acetic acid with methanol to form recyclable methyl acetate and water.

The need remains for improving the recovery of ethanol from a crude product obtained by reducing alkanoic acids, such as acetic acid, and/or other carbonyl group-containing compounds.

SUMMARY OF THE INVENTION

According to a first embodiment, the present invention is directed to a process for producing ethanol, comprising the steps of hydrogenating acetic acid in a first reactor to form a crude ethanol product comprising ethanol, acetic acid, and water, separating a dilute acid stream comprising acetic acid and water from the crude ethanol product, reacting the acetic acid from the dilute acid stream with methanol in an esterification unit to produce a methyl acetate stream comprising methyl acetate, and producing acetic acid from the methyl acetate in a second reactor.

According to a second embodiment, the present invention is directed to a process for producing ethanol, comprising the steps of hydrogenating acetic acid in a reactor to form a crude ethanol product comprising ethanol, acetic acid, and water, separating at least a portion of the crude ethanol product in a first column into a first distillate comprising ethanol and a first residue comprising acetic acid and water, reacting acetic acid from the first residue and methanol in a second column to produce a second distillate comprising methyl acetate and a second residue comprising water, and introducing at least a portion of the methyl acetate from the second distillate to a carbonylation reactor for producing acetic acid.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
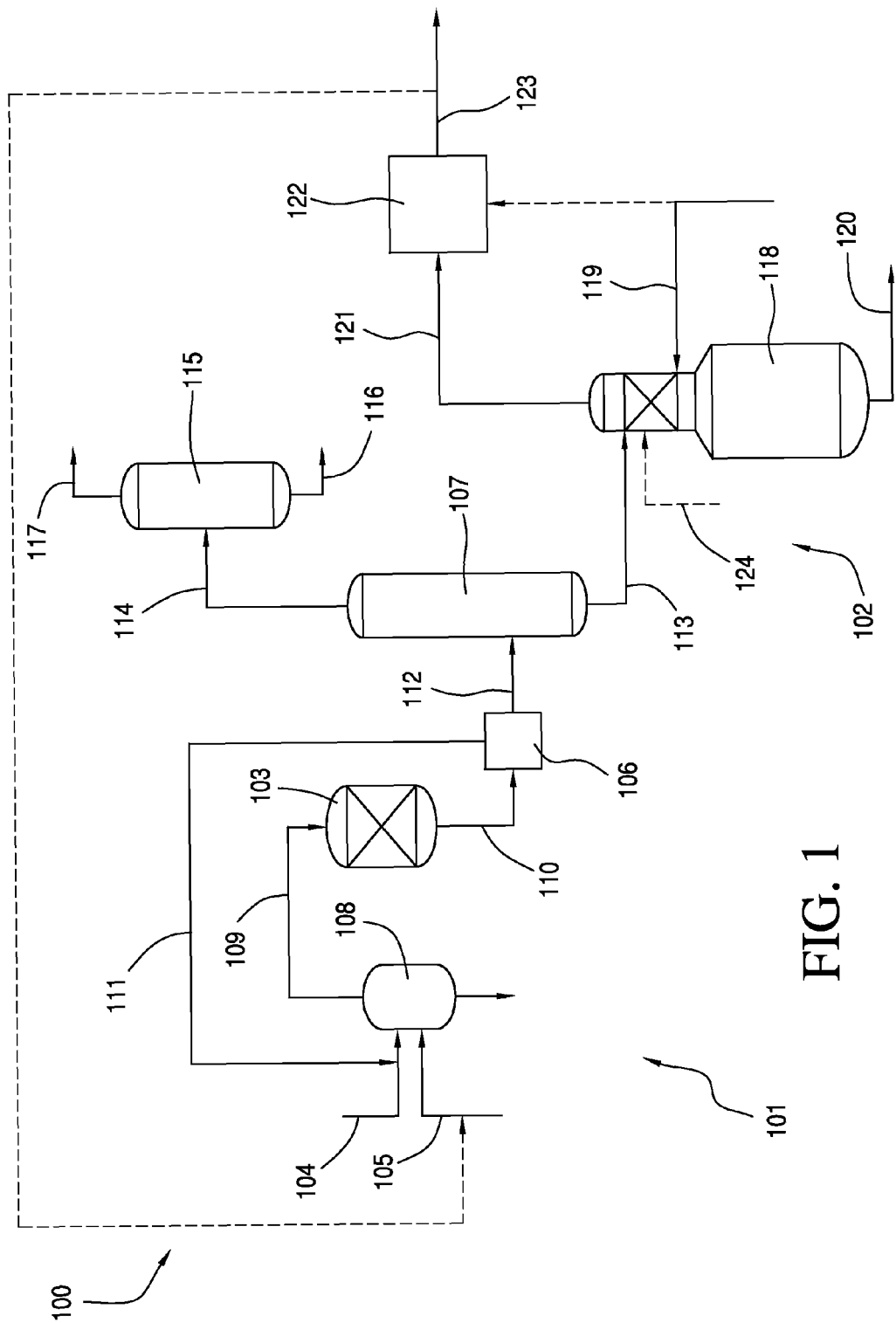
FIG. 1 is a schematic diagram of an acetic acid reduction system for an ethanol production process in accordance with one embodiment of the present invention.

The present invention relates to processes for recovering ethanol produced by hydrogenating acetic acid in the presence of a catalyst. The hydrogenation reaction produces a crude ethanol product that comprises ethanol, water, ethyl acetate, unreacted acetic acid, and other impurities. To improve operating efficiencies, the processes of the present invention involve separating the crude ethanol product into a dilute acid stream comprising water and unreacted acetic acid and an ethanol product stream. While it may be possible to separate acetic acid from the dilute acid stream, it may be more beneficial to recover the acetic acid by reacting it with methanol to form methyl acetate. The resulting methyl acetate beneficially may be easier to separate from the water in the dilute acid stream than acetic acid, resulting in an overall improved separation process. Additionally, the methyl acetate may optionally be fed to a reactor, e.g., a carbonylation reactor, for the production of acetic acid, which may, in turn, be used as a feedstock for the ethanol synthesis reaction.

Recovery of acetic acid from the dilute acid stream through a methyl acetate intermediate according to the processes of the present invention may be desirable when the dilute acid stream comprises from about 2 to about 60 wt. % acetic acid, although the present invention is not limited to such dilute acid streams. At lower concentrations, it may be preferred to neutralize and dispose of the dilute acid stream in a waste water treatment system. At greater concentrations, it may be preferred to recycle the acetic acid to the reaction process, optionally after removing some or all of the water therefrom.

In one embodiment, substantially all of the unreacted acetic acid is recovered in the dilute acid stream. By removing substantially all of the unreacted acetic acid from the crude ethanol product, the process, in some aspects, advantageously does not require further separation of acetic acid from the ethanol product stream. In this aspect, the ethanol product stream may contain some acetic acid, preferably in an amount less than 0.2 wt. %, less than 0.1 wt. % or less than 0.05 wt. %, and preferably only a trace amounts of acetic acid, such as an amount less than 100 wppm, less than 75 wppm or less than 50 wppm.

In some embodiments, the dilute acid stream is substantially free of ethanol or ethyl acetate. In this aspect, for example, the dilute acid stream may comprise less than 1 wt. % ethanol or ethyl acetate, collectively, e.g., less than 0.005 wt. %.

According to embodiments of the present invention, the acetic acid present in the dilute acid stream is reacted with methanol in an esterification unit to produce methyl acetate. In some embodiments, the esterification unit comprises a reactor coupled to one or more distillation columns. In other embodiments, the esterification unit comprises a reactive distillation column (also referred to herein as the second column) comprising a reaction section and a distillation section, to produce a distillate stream comprising methyl acetate and a residue stream comprising water. Reactive distillation columns for use with the present invention preferably comprise an ion exchange resin bed, an acidic catalyst, or a combination thereof. Non-limiting examples of ion exchange resins suitable for use in the present invention include macroporous strong-acid cation exchange resins such as those from the Amberlyst® series distributed by Rohm and Haas (e.g., Amberlyst 15®, Amberlyst 35®, and Amberlyst 36®). Additional ion exchange resins suitable for use in the present invention are disclosed in U.S. Pat. Nos. 4,615,806, 5,139,981, and 7,588,690, the entireties of which are incorporated herein by reference. In another embodiment, an acid is added to the second column to catalyze the esterification reaction. In this aspect, the acid may be selected from the group consisting of sulfuric acid, phosphoric acid, sulfonic acids, heteropolyacids, and combinations thereof. In other embodiments, acid catalysts include zeolites and supports treated with mineral acids and heteropolyacids.

As indicated above, acetic acid from the dilute acid stream is reacted with methanol to form methyl acetate. The methanol is preferably fed to the reactive distillation column in a counter-current manner to facilitate the production of methyl acetate.

The process parameters for the esterification step may vary widely depending, for example, on the catalyst employed and the ester being formed. In one embodiment, the reactive distillation column operates at a base temperature of from 100° C. to 150° C., e.g., from 100° C. to 130° C., or from 100° C. to 120° C. In terms of pressure, the reactive distillation column may be operated at atmospheric pressure, subatmospheric pressure, or superatmospheric pressure. For example, in some embodiments, the reactive distillation column operates at a pressure of from 50 kPa to 500 kPa, e.g., from 50 kPa to 400 kPa, or from 50 kPa to 200 kPa.

The feed rate of the dilute acid stream, or a portion thereof, to the second column may be adjusted based on the mole ratio of acetic acid to methanol being fed to the second column. For example, in some embodiments, the mole ratio of acetic acid to methanol fed to the reactive distillation column is from 1:1 to 1:15, e.g., from 1:1 to 1:5, or from 1:1 to 1:2. The methanol is preferably provided in excess relative to the acetic acid in the dilute acid stream so that the acetic acid is substantially reacted out of the dilute acid stream rendering a separate acetic acid separation step unnecessary.

According to a preferred embodiment, at least a portion of the distillate stream comprising methyl acetate is fed to a second reactor for producing acetic acid, which may, in turn, be used as a feedstock for the ethanol synthesis reaction. In some embodiments, the distillate stream may be condensed, processed, or otherwise refined, prior to being fed to the second reactor.

In some embodiments, the second reactor is a carbonylation unit for the catalyzed carbonylation of methanol with carbon monoxide. Conventional commercial processes for carbonylating methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105, the entirety of which is incorporated herein by reference.

In some embodiments, at least a portion of the distillate comprising methyl acetate may be fed to a hydrogenolysis reactor to produce one or more alcohols. At least a portion of the resulting alcohol(s) can then be recycled to the reactive distillation column, the crude ethanol product stream, the ethanol product stream, the second reactor, or a combination thereof. Optionally, in this aspect, a first portion of the distillate comprising methyl acetate is directed to the second reactor for production of acetic acid and a second portion of the distillate is reduced to form an alcohol product stream, at least a portion of which may be recycled to the reactive distillation column, the crude ethanol product stream, the ethanol product stream, the second reactor, or a combination thereof.

The residue stream of the second column typically will comprise water and preferably is substantially free of acetic acid. In some exemplary embodiments, the residue stream comprises at least 95 wt. % water, at least 98 wt. % water, or at least 99 wt. % water. The residue stream may comprise less than 5 wt. % acetic acid, less than 1 wt. % acetic acid, or less than 0.1 wt. % acetic acid. When the residue stream comprises an acid, the acid may be neutralized, and the resulting stream may be directed to a waste water treatment facility for disposal.

By removing a relatively large portion of the water and essentially all of the acetic acid from the crude ethanol product, in one embodiment, the process beneficially reduces the energy required for additional acetic acid removal steps since less acetic acid will be contained in the ethanol-containing distillate of the first column, and less water is distilled overhead in the first column.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor foam may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include siliceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0.1 to 90 | 1 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery

Figure 2:
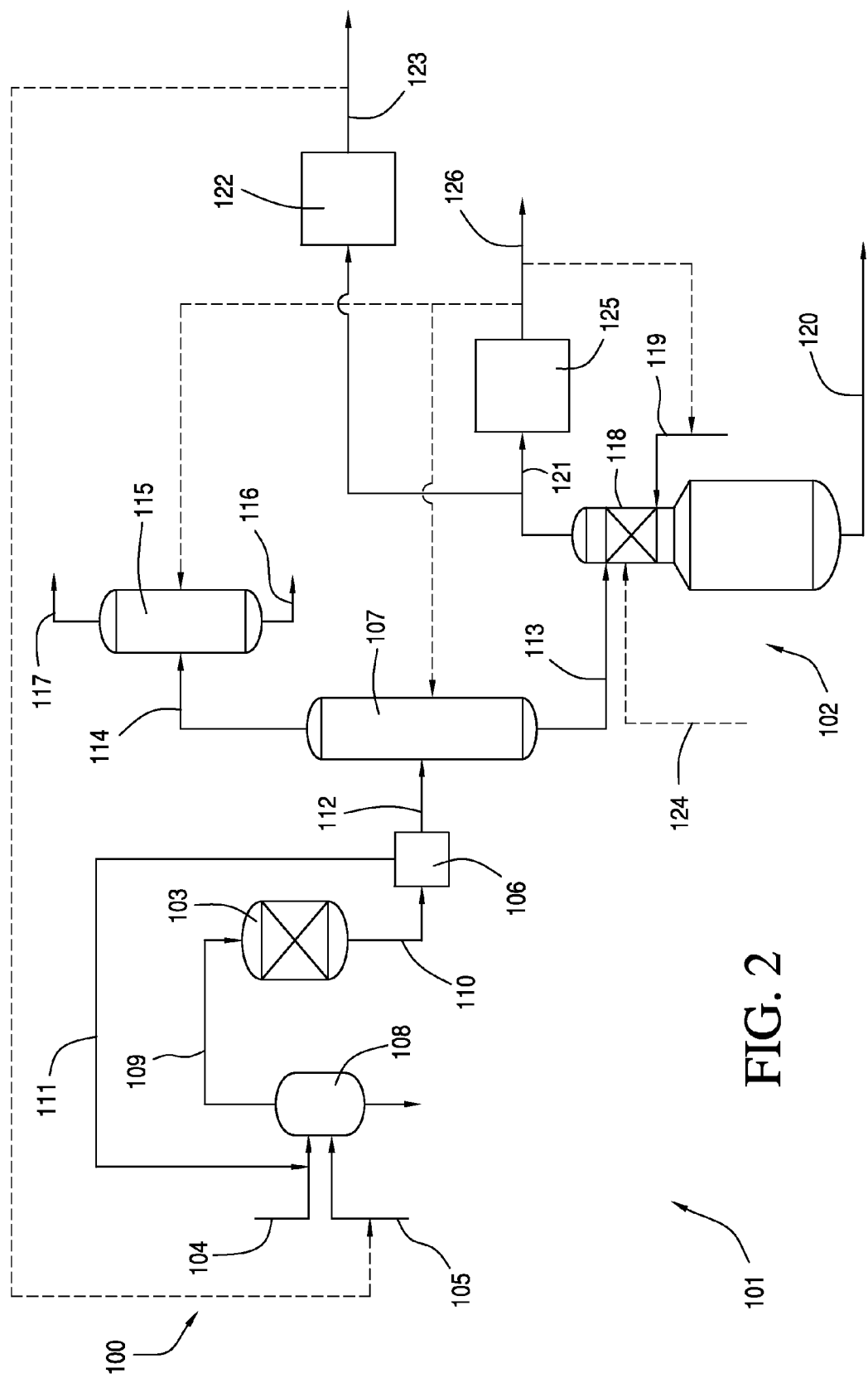
FIG. 2 is a schematic diagram of an acetic acid reduction system for an ethanol production process in accordance with one embodiment of the present invention.

Exemplary ethanol recovery systems having esterification units in accordance with embodiments of the present invention are shown in FIGS. 1-2. According to FIG. 1, hydrogenation system 100 provides a suitable hydrogenation reactor and a process for separating acetic acid from a crude ethanol product stream. System 100 comprises reaction zone 101 and separation zone 102. Reaction zone 101 comprises reactor 103, hydrogen feed line 104 and acetic acid feed line 105. Separation zone 102 comprises a first column 107, and a second column 118.

Hydrogen and acetic acid are fed to a vaporizer 108 via lines 104 and 105, respectively, to create a vapor feed stream in line 109 that is directed to reactor 103. In one embodiment, lines 104 and 105 may be combined and jointly fed to the vaporizer 108. The temperature of the vapor feed stream in line 109 is preferably from 100° C. to 350° C., e.g., from 120° C. to 310° C. or from 150° C. to 300° C. Any feed that is not vaporized is removed from vaporizer 108 and may be recycled or discarded thereto. In addition, although line 109 is shown as being directed to the top of reactor 103, line 109 may be directed to the side, upper portion, or bottom of reactor 103. Further modifications and additional components to reaction zone 101 and separation zone 102 are described below.

Reactor 103 contains the catalyst that is used in the hydrogenation of the carboxylic acid, preferably acetic acid, to make ethanol. In one embodiment, one or more guard beds (not shown) may be used upstream of the reactor, optionally upstream of vaporizer 108, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 110.

The crude ethanol product stream in line 110 may be condensed and fed to a separator 106, which, in turn, forms a vapor stream 111 and a liquid stream 112. The separator 106 may comprise a flasher or a knockout pot. The separator 106 may operate at a temperature of from 20° C. to 250° C., e.g., from 30° C. to 225° C. or from 60° C. to 200° C. The pressure of separator 106 may be from 50 kPa to 2000 kPa, e.g., from 75 kPa to 1500 kPa or from 100 kPa to 1000 kPa. In another embodiment, the temperature and/or pressure of the separator 106 may be similar to the temperature and/or pressure of the reactor 103. Optionally, the crude ethanol product in line 110 may pass through one or more membranes to separate hydrogen and/or other non-condensable gases prior to entering separator 106.

The vapor stream 111 exiting separator 106 may comprise hydrogen and hydrocarbons, and may be purged and/or returned to reaction zone 101. As shown, vapor stream 111 is combined with the hydrogen feed 104 and co-fed to vaporizer 108. In some embodiments, the returned vapor stream 111 may be compressed before being combined with hydrogen feed 104.

The liquid stream 112 from separator 106 is withdrawn and pumped to the side of first column 107, also referred to as an "acid separation column." In one embodiment, the contents of liquid stream 112 are substantially similar to the crude ethanol product obtained from the reactor, except that the composition has been depleted of hydrogen, carbon dioxide, methane and/or ethane, which are preferably removed by the separator 106. Accordingly, liquid stream 112 may also be referred to as a crude ethanol product. Exemplary components of liquid stream 112 are provided in Table 2. It should be understood that liquid stream 112 may contain other components, not listed in Table 2.

TABLE 2

COLUMN FEED COMPOSITION
(Liquid Stream 112)

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 40 | 5 to 30 | 10 to 30 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Liquid stream 112 is introduced in the or middle portion of first column 107. In first column 107, water and unreacted acetic acid, along with any other heavy components, if present, are removed from liquid stream 112 and are withdrawn, preferably continuously, as a first residue in line 113. First column 107 also forms a first distillate, which is withdrawn in line 114, and which may be condensed and refluxed, for example, at a ratio of from 10:1 to 1:10, e.g., from 3:1 to 1:3 or from 1:2 to 2:1.

When column 107 is operated under about 170 kPa, the temperature of the residue exiting in line 113 preferably is from 90° C. to 130° C., e.g., from 95° C. to 120° C. or from 100° C. to 115° C. The base of first column 107 may be maintained at a relatively low temperature to withdraw a first residue stream 113 comprising both water and acetic acid, thereby providing an energy efficiency advantage. The temperature of the first distillate 114 exiting in line 114 preferably is from 60° C. to 90° C., e.g., from 65° C. to 85° C. or from 70° C. to 80° C. In some embodiments, the pressure of first column 107 may range from 0.1 kPa to 510 kPa, e.g., from 1 kPa to 475 kPa or from 1 kPa to 375 kPa. Exemplary compositions for the first distillate 114 and first residue 113 streams for first column 107 are provided in Table 3 below. It should also be understood that the first distillate and first residue may also contain other components, not listed in Table 3. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN 107

|  | Conc. (wt. %) | Conc. (wt. %) | Conc. (wt. %) |
|---|---|---|---|
| First Distillate | | | |
| Ethanol | 20 to 90 | 30 to 85 | 50 to 85 |
| Water | 4 to 25 | 5 to 20 | 6 to 17 |
| Acetic Acid | <1 | 0.001 to 1 | 0.01 to 0.5 |
| Ethyl Acetate | <60 | 5 to 40 | 8 to 45 |
| Acetaldehyde | <10 | 0.001 to 5 | 0.01 to 4 |
| Acetal | <4.0 | <3.0 | <2.0 |
| Acetone | <0.05 | 0.001 to 0.03 | 0.01 to 0.025 |
| First Residue | | | |
| Acetic Acid | <90 | 1 to 50 | 2.5 to 40 |
| Water | 10 to 100 | 45 to 98 | 60 to 97 |
| Ethanol | <1 | <0.9 | <0.5 |

In one embodiment, at high conversions of greater than 95%, the acetic acid concentration in the residue may be less than 20 wt. %, e.g., from 0.5 to 15 wt. % or from 1 to 5 wt. %.

Some species, such as acetals, may decompose in column 107 such that very low amounts, or even no detectable amounts, of acetals remain in the distillate or residue. In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This equilibrium may be regulated using the residence time and/or temperature of crude ethanol product.

In some embodiments of the present invention the first distillate in line 114 may further comprise ethyl acetate and acetaldehyde. As shown in FIG. 1, a light ends column 115 (also referred to herein as a third column), may separate the first distillate in line 114 into a third distillate in line 117 and a third residue in line 116. In this embodiment, the third distillate in line 117 preferably comprises ethyl acetate and acetaldehyde, and the third residue in line 116 preferably comprises ethanol and water.

In FIG. 1, first distillate in line 114 is introduced to third column 115 preferably in the top part of column, e.g., top half or top third. Third column 115 may be a tray column or packed column. In one embodiment, third column 115 is a tray column having from 5 to 70 trays, e.g., from 15 to 50 trays or from 20 to 45 trays. As one example, when a 30 tray column is utilized in a column without water extraction, line 114 is introduced preferably at tray 2.

Optionally, the third column may be an extractive distillation column. Suitable extractive agents may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. In another aspect, the extractive agent may be an aqueous stream comprising water. If the extraction agent comprises water, the water may be obtained from an external source or from an internal return/recycle line from one or more of the other columns. Generally, the extractive agent is fed above the entry point of the first distillate in line 114. When extractive agents are used, a suitable recovery system, such as a further distillation column, may be used to remove the extractive agent and recycle the extractive agent.

Although the temperature and pressure of third column 115 may vary, when at about 20 kPa to 70 kPa, the temperature of the third residue exiting in line 116 preferably is from 40° C. to 100° C., e.g., from 60° C. to 85° C. or from 75° C. to 100° C. The temperature of the third distillate exiting in line 117 preferably is from 30° C. to 55° C., e.g., from 35° C. to 60° C. or from 45° C. to 55° C. Third column 115 may operate at a reduced pressure, near or at vacuum conditions, to further favor separation of ethyl acetate and ethanol. In other embodiments, the pressure of third column 115 may range from 20 kPa to 510 kPa, e.g., from 70 kPa to 475 kPa or from 100 kPa to 375 kPa. Exemplary components for the distillate and residue compositions for the third column 115 are provided in Table 4, below. It should be understood that the distillate and residue may also contain other components, not listed in Table 4.

TABLE 4

THIRD COLUMN 115

|  | Conc. (wt. %) | Conc. (wt. %) | Conc. (wt. %) |
|---|---|---|---|
| Third Distillate | | | |
| Ethyl Acetate | 5 to 90 | 10 to 80 | 15 to 75 |
| Acetaldehyde | 5 to 60 | 10 to 50 | 15 to 45 |
| Ethanol | 5 to 60 | 10 to 50 | 15 to 45 |
| Water | <20 | 0.01 to 10 | 0.1 to 5 |

TABLE 4-continued

THIRD COLUMN 115

| | Conc. (wt. %) | Conc. (wt. %) | Conc. (wt. %) |
|---|---|---|---|
| Third Residue | | | |
| Ethanol | 40 to 98 | 50 to 95 | 60 to 90 |
| Water | <60 | 0.5 to 50 | 0.1 to 30 |
| Ethyl Acetate | <1 | 0.001 to 2 | 0.001 to 0.5 |
| Acetic Acid | <0.5 | <0.01 | 0.001 to 0.01 |

The weight ratio of ethanol in the third residue to ethanol in the third distillate preferably is at least 2:1, e.g., at least 5:1, at least 8:1, at least 10:1 or at least 15:1. The weight ratio of ethyl acetate in the third residue to ethyl acetate in the third distillate preferably is less than 0.4:1, e.g., less than 0.2:1 or less than 0.1:1. It should be understood that when an extractive agent is used, the composition of the third residue would also include the extractive agent.

The columns shown in FIGS. 1-2 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

As discussed above, according to the present invention, unreacted acetic acid in the first residue stream 113 (also referred to as the dilute acid stream) is directed to second column 118 for esterification. In some embodiments, the dilute acid stream 113 may comprise at least 85% of the acetic acid from the crude ethanol product stream 112, e.g., at least 90% and more preferably at least 99%. In terms of ranges, the dilute acid stream optionally comprises from 85% to 99.5% or from 90% to 99.99% of the unreacted acetic acid from the crude ethanol product stream. In some embodiments, the dilute acid stream comprises from 2 to 60 wt. % acetic acid and from 40 to 98 wt. % water. In one embodiment, substantially all of the unreacted acetic acid is reacted out of dilute acid stream 113. In one embodiment, substantially all of the unreacted acetic acid is recovered in the first residue stream 113. By removing substantially all of the unreacted acetic acid from the crude ethanol product stream 112, the process, in some aspects, advantageously does not require further separation of acetic acid from the ethanol.

In some embodiments, the dilute acid stream 113 is substantially free of ethanol or ethyl acetate. In this aspect, the dilute acid stream 113 comprises less than 1 wt. % ethanol or ethyl acetate, e.g., less than 0.005 wt. %.

According to embodiments of the present invention, the acetic acid present in dilute acid stream 113 is reacted with methanol stream 119 in an esterification unit to produce methyl acetate. In some embodiments, the esterification unit comprises a reactor coupled to one or more distillation columns. In other embodiments, the esterification unit comprises a reactive distillation column (also referred to herein as the second column) comprising a reaction section and a distillation section, to produce a distillate stream comprising methyl acetate and a residue stream comprising water. Reactive distillation columns for use with the present invention preferably comprise an ion exchange resin bed, an acidic catalyst, or a combination thereof.

Referring to FIG. 1, the esterification unit is shown as a reactive distillation column, referred to herein as second column 118. Dilute acid stream 113 is co-fed to second column 118 with methanol stream 119, to produce a second distillate stream 121 comprising methyl acetate and a second residue stream 120 comprising water. In another embodiment, not shown, methanol stream 119 may be added directly to first residue stream 113 prior to being introduced into second column 118. FIG. 1 shows methanol feed stream 119 being fed to second column 118 at a point below where dilute acid stream 113 is fed to the column. In other embodiments, methanol feed stream may be fed to second column 118 at the same level, or at a point above where dilute acid stream 113 is fed to the column.

When second column 118 is a reactive distillation column, as shown in FIG. 1, second column 118 comprises an ion exchange resin bed, an acidic catalyst, or combinations thereof. Non-limiting examples of ion exchange resins suitable for use in the present invention include macroporous strong-acid cation exchange resins such as those from the Amberlyst® series distributed by Rohm and Haas (e.g., Amberlyst 15®, Amberlyst 35®, and Amberlyst 36®). Additional ion exchange resins suitable for use in the present invention are disclosed in U.S. Pat. Nos. 4,615,806, 5,139,981, and 7,588,690, the entireties of which are incorporated herein by reference. In another embodiment, an acid is added to the second column to catalyze the esterification reaction. In this aspect, the acid may be selected from the group consisting of sulfuric acid, phosphoric acid, sulfonic acids, heteropolyacids, other mineral acids and a combination thereof.

In other embodiments, acid catalysts include zeolites and supports treated with mineral acids and heteropolyacids.

When an acid catalyst is used, e.g., sulfuric acid, the acid catalyst is fed via line 124 to column 118. FIGS. 1 and 2 show acid catalyst feed 124 enters second column 118 at a level below first residue stream 113. However, in some embodiments, acid catalyst feed 124 may enter second column 118 at a level above where first residue stream 113 enters second column 118, or at the same level.

In some embodiments, when an ion exchange resin is present in second column 118, dilute acid stream 113 may be fed to a guard bed (not shown) prior to being fed to second column 118. In one embodiment, the guard bed comprises an ion exchange resin, such as those disclosed above. While not being bound to any particular theory, the guard bed removes one or more corrosive metals present in the dilute acid stream 113, thereby minimizing the deactivation of any ion exchange resin catalytic sites in the ion exchange resin present in the second column 118.

The operating parameters of second column 118 may be varied to achieve a desired composition in second distillate 121 and/or residue stream 120. For example, in some embodiments, temperature, pressure, feed rates, and residence times can be varied to increase conversion of acetic acid to an ester, decrease the formation of impurities, achieve more efficient separation, reduce energy consumption, or combinations thereof.

In one embodiment, second column 118 operates at a base temperature of from 100° C. to 150° C., e.g., from 100° C. to 130° C., or from 100° C. to 120° C. In terms of pressure, the reactive distillation column may be operated at atmospheric pressure, subatmospheric pressure, or superatmospheric pressure. For example, in some embodiments, the reactive distillation column operates at a pressure of from 50 kPa to 500 kPa, e.g., from 50 kPa to 400 kPa, or from 50 kPa to 200 kPa.

In some embodiments, the feed rates of acetic acid and alcohol to second column 118 may be adjusted to control the mole ratio of acetic acid to alcohol being fed to the second column 118. For example, in some embodiments, the mole ratio of acetic acid to methanol fed to the reactive distillation column is from 1:1 to 1:15, e.g., from 1:1 to 1:5, or from 1:1 to 1:2.

The residence time of the second column may impact acetic acid conversion. In some embodiments, for example, the residence time in the second column is from 1 to 5 hours, e.g., from 1 to 3 hours, or less than 1 hour.

The processes of the present invention preferably provide for a high conversion of acetic acid to ester(s). In some embodiments, for example, at least 80%, at least 90% or at least 98% of the acetic acid in the second residue 113 is converted to an ester.

The second distillate 121 exiting the second column 118 preferably comprises at least 15 wt. % methyl acetate, preferably at least 35 wt. % methyl acetate, or more preferably at least 65 wt. % methyl acetate. In teens of ranges, the second distillate 121 from the second column 118 may comprise methyl acetate in an amount from 15 to 99 wt. %, e.g., from 35 to 90 wt. % or from 50 to 90 wt. %.

When excess methanol is reacted with the acetic acid from the dilute acid stream, some methanol also may be present in the second distillate 121. Thus, the second distillate 121 may comprise methanol in an amount from 0.1 to 80 wt. %, e.g., from 10 to 60 wt. %, or from 1 to 30 wt. %.

Exemplary compositions for second distillate 121 and second residue 120 from the second column 118 are provided in Table 5, below. It should also be understood that the distillate and residue may also contain other components, not listed in Table 5.

TABLE 5

SECOND COLUMN 118

| | Conc. (wt. %) | Conc. (wt. %) | Conc. (wt. %) |
|---|---|---|---|
| Second Distillate | | | |
| Methyl Acetate | >15 | >35 | >65 |
| Water | <10 | <10 | <10 |
| Acetic Acid | <1 | <0.5 | <0.5 |
| Methanol | <80 | <60 | <30 |
| Ether | <1000 wppm | <750 wppm | <500 wppm |
| Second Residue | | | |
| Acetic Acid | <5 | <3 | <1 |
| Water | >90 | >95 | >99 |
| Methanol | <1 | <0.5 | <0.1 |

Some impurities, such as dimethyl ether may form over the course of the reaction in second column 118. These impurities may be present in very low amounts, or even no detectable amounts, in the second distillate stream 121. In some embodiments, the second distillate 121 comprises less than 1000 wppm dimethyl ether, e.g., less than 750 wppm, or less than 500 wppm.

As described above, the second distillate stream 121 is fed to a second reactor for producing acetic acid, which may in turn, be used as a feedstock for the ethanol synthesis reaction. In some embodiments, second distillate stream 121 may optionally be condensed, processed, or refined, prior to being fed to the second reactor. In FIG. 1, the second distillate 121 is shown being fed to a second reactor that is a methanol carbonylation system 122 to produce an acetic acid stream 123. At least a portion of acetic acid stream 123 may be fed to acetic acid feed 105. While not being bound to any particular theory, feeding the methyl acetate from second distillate 121 to a methanol carbonylation reactor advantageously increases the production of acetic acid in the reactor, controls the water content of the reaction medium, or a combination thereof.

The present invention may be applied in any methanol carbonylation process. Exemplary carbonylation systems that may be used with embodiments of the present invention include those described in U.S. Pat. Nos. 7,223,886; 7,005,541; 6,657,078; 6,339,171; 5,731,252; 5,144,068; 5,026,908; 5,001,259; and 4,994,608, and U.S. Pub. Nos. 2008/0287706; 2008/0293966; 2009/0107833; and 2009/0270651, the entire contents and disclosures of which are hereby incorporated by reference.

Carbonylation system 122 preferably comprises a reaction zone, which includes a reactor, a flasher and optionally a reactor recovery unit. In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt.

Suitable catalysts include Group VIII catalysts, e.g., rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volume*, Chapter 2.1, p. 27-200, (1$^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in U.S. Pat. Nos. 5,942,460; 5,932,764; 5,883,295; 5,877,348; 5,877,347; and 5,696,284, which are hereby incorporated by reference.

A halogen co-catalyst/promoter is generally used in combination with the Group VIII metal catalyst component. Methyl iodide is a preferred halogen promoter. Preferably, the concentration of halogen promoter in the reaction medium ranges from 1 wt. % to 50 wt. %, and preferably from 2 wt. % to 30 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in the reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa Acetic acid is typically manufactured in a liquid phase reaction at a temperature from about 150° C. to about 200° C. and a total pressure of from about 2 to about 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

In some embodiments, water is introduced to reactor together with or separately from other components of the reaction medium. Water may be separated from the other components of reaction product withdrawn from reactor and may be recycled in controlled amounts to maintain the required concentration of water in the reaction medium. Preferably, the concentration of water maintained in the reaction medium ranges from 0.1 wt. % to 16 wt. %, e.g., from 1 wt. % to 14 wt. %, or from 1 wt. % to 3 wt. % of the total weight of the reaction product.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt % to 30 wt. %, e.g., from 1 wt. % to 25 wt. %, or from 2 wt. % to 20 wt. %; and the lithium iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

In the embodiment depicted in FIG. 2, at least a portion of the second distillate stream 121 is reduced in a hydrogenolysis reactor 125, to produce an alcohol product stream 126. In one embodiment, ethanol is recovered from alcohol product stream 126 and a portion of the ethanol is recycled to ethanol production process. In some embodiments, a portion of the ethanol is fed to crude ethanol product stream 112, first column 107, second column 112, light ends column 115, or combinations thereof. In other embodiments, methanol is recovered from alcohol product stream 126 and a portion of the methanol is fed a carbonylation unit for producing acetic acid, second column 118, or combinations thereof.

The second residue stream 120 of second column 118 comprises water and is preferably substantially free of acetic acid. In some embodiments second residue stream 120 comprises at least 95 wt. % water, e.g., preferably at least 98 wt. % water, or more preferably at least 99 wt. % water. In other embodiments, second residue stream 120 comprises less than 5 wt. % acetic acid, e.g., preferably less than 1 wt. % acetic acid, or more preferably less than 0.1 wt. % acetic acid. Second residue stream 120 may be treated to neutralize acidic components or disposed to a waste water treatment facility.

In some embodiments, the process further comprises removing and/or transferring energy from one or more streams of the present invention. For example, in one embodiment, energy may be removed from dilute acid stream 113 and transferred to the methanol feed stream 119 via a heat exchanger. In another embodiment, energy is transferred from the second residue 120 to the methanol feed stream 119 via a heat exchanger. In other embodiments, energy is removed from the dilute acid stream 113 and transferred to one or more columns and/or process streams of the carbonylation system 122.

The finished ethanol composition produced by the embodiments of the present invention, e.g., in third residue 116 (or a derivative stream thereof), may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

We claim:

1. A process for producing ethanol, comprising the steps of:
    hydrogenating acetic acid in a first reactor to form a crude ethanol product comprising ethanol, acetic acid, and water;
    separating the crude ethanol product to yield an ethanol product and a dilute acid stream comprising from 2 to 60 wt. % acetic acid and from 40 to 98 wt. % water, wherein the dilute acid stream comprises substantially all of the acetic acid from the crude ethanol product;
    introducing the dilute acid stream and methanol in an esterification unit to produce a methyl acetate stream comprising methyl acetate and a water stream that is substantially free of acetic acid; and
    introducing the methyl acetate stream into a carbonylation unit to produce acetic acid.

2. The process of claim 1, further comprising introducing at least a portion of the acetic acid produced by the carbonylation unit into the first reactor.

3. The process of claim 1, wherein the esterification unit comprises a reactive distillation column.

4. The process of claim 3, wherein the dilute acid stream and the methanol are fed to the reactive distillation column at a mole ratio of acetic acid to methanol of from 1:1 to 1:15.

5. The process of claim 3, wherein the reactive distillation column comprises an ion exchange resin bed.

6. The process of claim 3, wherein the reactive distillation column comprises an acidic catalyst.

7. The process of claim 6, wherein the acidic catalyst comprises sulfuric acid.

8. The process of claim 1, wherein the methyl acetate stream comprises at least 15 wt. % methyl acetate.

9. The process of claim 1, wherein the methyl acetate stream comprises less than 80 wt % methanol.

10. The process of claim 1, wherein the methyl acetate stream comprises less than 1000 wppm dimethyl ether.

11. The process of claim 1, further comprising condensing the methyl acetate stream.

12. The process of claim 1, wherein methanol is fed to the carbonylation unit.

13. The process of claim 1, further comprising reducing at least a portion of the methyl acetate from the methyl acetate stream to produce an alcohol product stream.

14. The process of claim 13, further comprising recovering ethanol from the alcohol product stream and feeding at least a portion of the ethanol to the crude ethanol product.

15. The process of claim 13, further comprising recovering methanol from the alcohol product stream and reacting the methanol with the acetic acid in the dilute acid stream.

16. The process of claim 13, further comprising recovering methanol from the alcohol product stream and feeding at least a portion of the methanol to the carbonylation reactor.

17. A process for producing ethanol, comprising the steps of:
    hydrogenating acetic acid in a reactor to form a crude ethanol product comprising ethanol, acetic acid, and water;
    separating at least a portion of the crude ethanol product in a first column into a first distillate comprising ethanol and a first residue comprising from 2 to 60 wt. % acetic acid and from 40 to 98 wt. % water wherein the first residue comprises substantially all of the acetic acid from the crude ethanol product;
    introducing the first residue and methanol in a second column to produce a second distillate comprising methyl acetate and a second residue comprising water; and
    introducing at least a portion of the methyl acetate from the second distillate to a carbonylation reactor for producing acetic acid.

18. A process for producing ethanol, comprising the steps of:
    hydrogenating acetic acid in a first reactor to form a crude ethanol product comprising ethanol, acetic acid, and water;

separating the crude ethanol product to yield an ethanol product and a dilute acid stream comprising from 2 to 60 wt. % acetic acid and from 40 to 98 wt. % water, wherein the dilute acid stream comprises substantially all of the acetic acid from the crude ethanol product;

introducing the dilute acid stream and methanol in an esterification unit to produce a methyl acetate stream comprising methyl acetate and a water stream that is substantially free of acetic acid;

reducing at least a portion of the methyl acetate from the methyl acetate stream to produce an alcohol product stream comprising methanol and ethanol;

separating ethanol from the alcohol product stream; and feeding at least a portion of the separated ethanol to the crude ethanol product.

* * * * *